US012690777B2

(12) United States Patent
Yermoshkin et al.

(10) Patent No.: US 12,690,777 B2
(45) Date of Patent: Jul. 28, 2026

(54) APPARATUS FOR MONITORING UTERINE CONTRACTIONS

(71) Applicant: KONINKLIJKE PHILIPS N.V., Eindhoven (NL)

(72) Inventors: Roman Yermoshkin, Stuttgart (DE); Markus Silvester Wohlschlager, Sindelfingen (DE); Hansjoerg Geywitz, Kusterdingen (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 828 days.

(21) Appl. No.: 17/920,950

(22) PCT Filed: May 6, 2021

(86) PCT No.: PCT/EP2021/062031
§ 371 (c)(1),
(2) Date: Oct. 24, 2022

(87) PCT Pub. No.: WO2021/228687
PCT Pub. Date: Nov. 18, 2021

(65) Prior Publication Data
US 2023/0165478 A1 Jun. 1, 2023

(30) Foreign Application Priority Data

May 11, 2020 (EP) ..................................... 20173830

(51) Int. Cl.
*A61B 5/03* (2006.01)
*A61B 5/00* (2006.01)
(Continued)

(52) U.S. Cl.
CPC ............ *A61B 5/033* (2013.01); *A61B 5/0205* (2013.01); *A61B 5/6823* (2013.01);
(Continued)

(58) Field of Classification Search
CPC ..... A61B 5/033; A61B 5/0205; A61B 5/6823; A61B 5/6831; A61B 5/6843; A61B 5/746; A61B 5/4343; A61B 5/4356
See application file for complete search history.

(56) References Cited

U.S. PATENT DOCUMENTS 3,945,373 A 3/1976 Tweed
5,871,499 A 2/1999 Hahn
(Continued)

FOREIGN PATENT DOCUMENTS

EP 3466329 A1 4/2019
JP 2003169780 A 6/2003
(Continued)

OTHER PUBLICATIONS

International Search Report Dated Aug. 4, 2021 For International Application No. PCT/EP2021/062031 Filed May 6, 2021.
(Continued)

*Primary Examiner* — Eric F Winakur

(57) ABSTRACT

An apparatus (10) is for use in monitoring uterine contractions. Means are provided for separately detecting (18) solid (e.g. flush) contact of at least a portion of a sensor unit (14) of the apparatus on the abdomen, and for a detecting (20) an initial starting pressure, or a baseline pressure, between the sensor unit and the abdomen. A controller (24) is arranged to first sense contact of said at least portion of the sensor unit on the abdomen, and then responsive to the contact detection, detect the starting pressure using an integrated pressure sensor. The same pressure sensor is preferably used for monitoring the uterine contractions. The starting pressure provides a direct or indirect measure or indication of the tension of a belt which is arranged in use to hold the apparatus against the abdomen of the subject. By sensing the starting pressure, for example directly responsive to abdomen contact being sensed, this initial pressure value, or derivative therefore, can be used as a direct or indirect indication of the belt tension.

15 Claims, 4 Drawing Sheets

10

(51) Int. Cl.
  *A61B 5/0205*      (2006.01)
  *A61B 5/024*      (2006.01)
(52) U.S. Cl.
  CPC .......... *A61B 5/6831* (2013.01); *A61B 5/6843*
          (2013.01); *A61B 5/746* (2013.01); *A61B*
          *5/02416* (2013.01); *A61B 2562/0238*
          (2013.01); *A61B 2562/0247* (2013.01)

(56)            References Cited

U.S. PATENT DOCUMENTS

| | | | | |
|---|---|---|---|---|
| 6,048,323 | A | 4/2000 | Hon | |
| 8,346,328 | B2 * | 1/2013 | Mannheimer | ........ A61B 5/6843 |
| | | | | 600/310 |
| 12,114,974 | B2 * | 10/2024 | Al-Ali | ................ A61B 5/14552 |

| | | | | |
|---|---|---|---|---|
| 2012/0277631 | A1 | 11/2012 | Maity | |
| 2017/0188920 | A1 * | 7/2017 | Ray | ................... A61B 5/14552 |
| 2017/0215747 | A1 | 8/2017 | Roovers | |

FOREIGN PATENT DOCUMENTS

| | | | |
|---|---|---|---|
| JP | 2008054890 | A | 3/2008 |
| RU | 134415 | U1 | 11/2013 |
| WO | 9919704 | A1 | 4/1999 |
| WO | 2017162686 | A1 | 9/2017 |

OTHER PUBLICATIONS

Smyth C.N., "Absolute Measurement of Intra-Amniotic Pressure by a new Instrument", Journal of Obstetrics and Gynaecology, pp. 59-66.

* cited by examiner

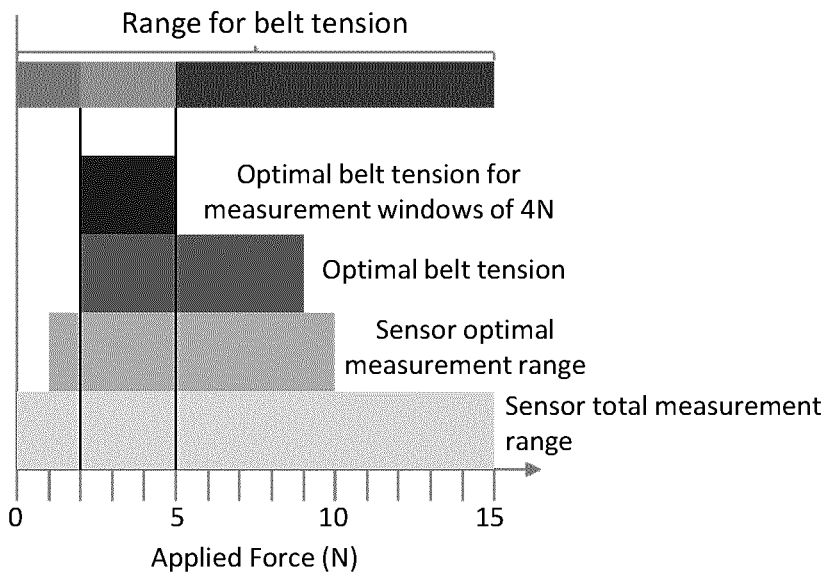
FIG. 5
FIG. 6
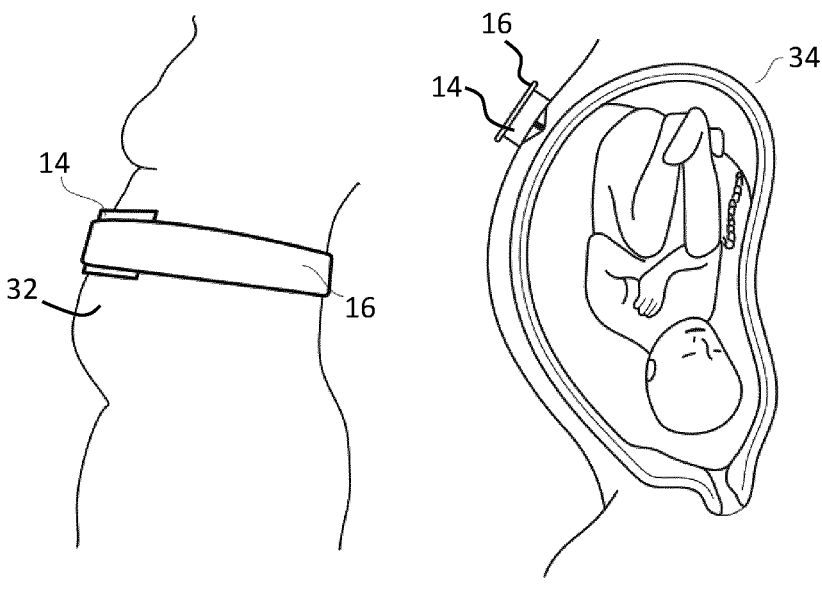
FIG. 7

APPARATUS FOR MONITORING UTERINE CONTRACTIONS

CROSS-REFERENCE TO PRIOR APPLICATIONS

This application is the U.S. National Phase application under 35 U.S.C. § 371 of International Application No. PCT/EP2020/062031, filed on May 6, 2021, which claims the benefit of European Application No. 20173830.9 filed on May 11, 2020. These applications are hereby incorporated by reference herein.

FIELD OF THE INVENTION

The present invention relates to an apparatus for monitoring uterine contractions, and a method for initializing the apparatus.

BACKGROUND OF THE INVENTION

Monitoring the uterine activity of a mother during labor and delivery is a standard measurement that usually accompanies the tracing of a fetal heart rate, which is often measured using ultrasound Doppler. In obstetrics, information about uterine contractions (such as a duration of a contraction, an intensity of a contraction, a waveform of a contraction) is important in the assessment of the wellbeing of a fetus during labor and delivery. For example, the interpretation of both the uterine activity and the fetal heart rate in a chronological sequence can assist medical personnel (such as doctors or caregivers) in providing the optimum treatment for the mother and the fetus.

A common technique for non-invasively deriving uterine contractions is to use a tocodynamometer (which may also be referred to as a toco). The tocodynamometer is placed on the abdominal wall of the mother and held in position with an elastic belt, which is looped around the belly of the mother. The tocodynamometer comprises a pressure sensor housed in a sensor housing. During a contraction of the uterus, tension changes of the uterine muscle occur and these changes are registered as a change in pressure force on a sensitive area of the pressure sensor, which is placed in the middle of the sensor housing. The sensitive area is surrounded by a stiff guard ring in order to reduce the influence of movement and breathing artefacts. A strain gauge element of the tocodynamometer translates the pressure force into an electrical signal.

U.S. Pat. No. 3,945,373 discloses another type of tocodynamometer for providing an electrical output related to body surface displacement of a patient. The tocodynamometer comprises a light interrupter that extends into a space between an emitter and detector to interrupt light passing from the emitter to the detector, where uterine contractions cause displacement of the light interrupter and change the amount of light from the emitter that is received by the detector.

US 2012/277631 describes a further example tocodynamometer. This example also uses an optical displacement sensor. A light emitter and an optical transducer is provided, as well as a reflector surface arranged to reflect at least part of the light emitted by the light emitter to the optical transducer. The reflector is coupled to a displacement member which contacts the mother's abdomen in use and moves responsive to movement of the abdomen. The movement modifies an intensity distribution of light reflected to the optical transducer.

The measurement unit of the pressure changes are typically implemented using a pressure sensor mechanically coupled with the abdomen via a skin-contact area at the base of the tocodynamometer device. The mechanical force (uterine activity, tension change of muscles) is measured by the sensor (i.e. strain gauge element, optical sensor etc.)

For optimal performance of the tocodynamometer, the sensing components of the device should be held in position against the abdomen with an appropriate tension of an elastic belt. The belt tension should ideally meet the following criteria:

1) The belt tension should not be too small, which might cause the loss of the physical contact between the abdomen and the sensor elements.
2) The belt tension should not be too large, which would cause the physical discomfort to the patient.
3) The mechanical force measured by the Toco sensor is directly influenced by the belt tension. When the Toco sensor is first applied to the abdomen, the force measured is the baseline of all further measurements. It is important that the baseline is within the operating range of the measurement sensor. The operating range may be defined as the measurement range with the best signal-to-noise performance, high linearity and/or other factors.

The belt tension may change over time due to:
body movements of the patient;
degradation of the belt elasticity;
attempts by medical personnel to increase the belt tension based on their experience;
loss of belt tension due to moisture, for example because the belt gets wet in the shower or bathtub.

If the toco device is attached to the abdomen with inappropriate belt tension, this can lead to inaccurate measurements.

For illustration, FIG. 1 illustrates a sample measurement signal either acquired from a tocodynamometer which either was applied to the abdomen with insufficient belt tension, or where there were no uterine contractions to detect. It is not possible to determine from the signal alone which of these two causes is responsible. Thus a low belt tension might be confused for an absence of any contractions which would have a detrimental clinical impact on the patient.

FIG. 2 illustrates a sample measurement signal for a case in which the belt tension has been increased during the measurement (resulting in the step change in the baseline visible near the beginning of the signal trace), therefore significantly reducing the measurement window. As a result, the uterine contraction measurements are clipped at the top of the graph. The baseline can be adjusted through post-processing to eliminate the clipping. However, the sensor at such high baseline pressure will not be operating in its optimal range, and thus sensitivity is likely to be reduced.

FIG. 3 illustrates a sample measurement signal as acquired by a tocodynamometer which was applied with the optimal belt tension. A strong signal is present in the measurement trace and with no clipping of the upper values.

Thus, it can be seen that the belt tension has a significant impact upon the quality and reliability of tocodynamometer measurements. Since tocodynamometer measurements are acquired over a medium to long time period (e.g. several hours), an inappropriately applied Toco sensor can lead to the loss of valuable patient information.

An approach to mitigating or eliminating this problem would therefore be of value.

SUMMARY OF THE INVENTION

The invention is defined by the claims.

According to examples in accordance with an aspect of the invention, there is provided an apparatus for monitoring uterine contractions of a subject, the apparatus comprising:

a sensor unit for placement against an abdomen of the subject;

a belt component arranged for holding a contact surface of the sensor unit in place against the abdomen;

a contact sensing means adapted to detect an engagement between the contact surface of the sensor unit and the abdomen of the subject;

a force or pressure sensing means adapted to detect a force or pressure between the abdomen and the sensor unit; and a controller, adapted to perform a procedure comprising:

detecting engagement between the contact surface of the sensor unit and the abdomen by the contact sensing means, responsive to said detection, acquiring a measure of a starting pressure or force between the abdomen and the sensor unit using the force or pressure sensing means, and determining whether a tension or application force of the belt component is in an optimum range by comparing said starting pressure with at least one pre-defined reference range.

The procedure may be termed an initialization or configuration or calibration procedure. It may be performed upon first mounting the apparatus to the user (i.e. on start-up), and optionally may be repeated during use of the apparatus for checking a belt tension.

The pre-defined reference range may be a reference range for the starting pressure or a derivative thereof, for example a baseline of the starting pressure.

The acquired measure of a starting pressure may be a pressure value, or a pressure signal covering a time window.

Embodiments of the invention are based on indirectly assessing the belt tension by means of an initial pressure measurement acquired as soon as the tocodynamometer device is attached to the abdomen. A starting pressure as soon as the device is mounted to the abdomen can be assumed to be indicative of a level of the belt tension, rather than for example contractions, since there has not yet been time for abdomen movements to couple to the pressure sensor. A timing of initial attachment to the body can be detected using a contact sensing means. Thus, by providing a sensing unit which incorporates both a contact sensor and a pressure sensor and which is configured to acquire an initial pressure measurement responsive to skin contact being detected, a reliable measure of belt tension is obtained.

This pressure measurement, or a derivative thereof can then be compared with a threshold or a reference range to assess whether it falls within an optimal operating range for the tocodynamometer, e.g. for the pressure sensor. This comparison of the starting pressure measure or a derivative thereof with the reference range is used to determine whether the belt tension is within its optimum range. If not, a response action can be triggered, for example alerting a user or discontinuing measurement until the tension is adjusted to an optimum level.

There may be a separate step of determining a measure of the belt tension based on the initial detected pressure (starting pressure), for example using an algorithm or conversion equation. In some cases the belt tension is taken to be equal to a baseline (i.e. offset) value of the acquired pressure measurement for example. The reference range may be a reference range for the belt tension, and the determination is performed based on comparison of the calculated belt tension with the reference range. The reference range may be a range for the measured initial pressure value itself, and where for example the reference range has been pre-determined so that if the starting pressure is within this reference range, then the belt tension can be known to be within its starting range. Thus in this case, the measured value of the starting pressure may itself be used for the further analysis, and be compared with a reference range. The starting pressure may be taken to be indicative of the starting belt tension for example.

Thus no 'optimum range' for the belt tension needs to be explicitly defined, separate from the reference range; determining whether the belt tension falls in an optimum range is fully achieved by use of the reference range and the starting pressure or force measurement. For example, the controller performs an assessment or analysis of the initial pressure measurement, based on use of the reference range, and based on the assessment derives a classification for the belt tension as either within an optimum range or outside of an optimum range. In some examples the reference range defines the optimum range for the belt tension, or is indirectly indicative or related thereto.

The apparatus may further comprise an ultrasound transducer unit comprising one or more ultrasound transducers. This can be used for detecting and monitoring fetal heart rate using Doppler ultrasound techniques.

Here, a separate step for detecting contact has a further benefit, since it is important that any transducer makes good acoustic contact with the abdomen for accurate heart rate detection. The pressure sensor alone cannot always provide a reliable indication of solid contact with the abdomen.

Further to the above, the controller may be configured to continuously monitor the belt tension even after pressure measurements for contraction monitoring have begun, and to create a response action in the event that the tension moves outside of an optimum range. This may for example be based on recurrently or continuously monitoring a pressure signal from the pressure sensing means and determining a baseline of the pressure signal, and taking the baseline value as indicative of the belt tension.

The controller may be further adapted to generate an information output indicative of whether the belt tension is within the optimum range, and communicating the output to a user output device.

The controller is preferably further adapted to monitor uterine contractions based on an output of the force or pressure sensing means. The same pressure sensing means (e.g. pressure sensor arrangement) is preferably used to monitor the uterine contractions as to acquire the initial pressure measurement for checking the belt tension.

In advantageous embodiments, monitoring the uterine contractions may be performed conditionally upon the belt tension falling within the optimum range. In other words, the controller may be configured to only perform the function of monitoring uterine contractions if the belt tension is within the pre-defined optimum range. This avoids acquiring contraction measurement information which may be inaccurate and thus may lead to incorrect clinical actions.

In accordance with one or more embodiments, responsive to a determination that the belt tension is not within the optimum range, an output may be generated for communication to a user output device for alerting a user. The user output device may include a display unit for example and/or one or more other sensory output devices.

There are different ways in which the contact sensing can be performed.

In accordance with one or more embodiments, the contact sensing means may be provided by the same component as the force or pressure sensing means (e.g. a pressure sensor such as a strain gauge or an optical based pressure sensor), and wherein engagement with the abdomen is detected based on detecting a change in the measured force or pressure exceeding a pre-defined threshold.

In accordance with a further set of embodiments, the sensor unit may comprise an additional component for detecting the contact.

For example, according to one set of embodiments, the sensor unit may comprise an optical sensor arrangement comprising a light source arranged to direct a light output from said contact surface into the skin of the subject and a light detector arranged to detect said light output at the contact surface after passage through the skin, and wherein the contact sensing means is provided by the optical sensor arrangement, contact being detected based on an output of the light detector.

In advantageous embodiments, the optical sensor element may be a PPG sensor, and wherein the controller is adapted to determine a pulse of the subject using an output of the PPG sensor. In other words, the sensor unit may incorporate an integrated PPG sensor which comprises a light source arranged to direct a light output from said contact surface into the skin of the subject and a light detector arranged to detect said light output at the contact surface after passage through the skin, and wherein the controller is adapted to use these components of the PPG sensor to detect the contact. This way, the number of parts can be minimized.

There are, furthermore, different ways of detecting the engagement with the abdomen using the optical sensor arrangement.

For example, in one set of embodiments, contact may be detected based on detection of the light output generated by the light source at the light detector. When this is detected, it means that the optical sensor arrangement must be in optical communication with the skin for the light to have coupled through the tissue of the subject to the light detector, and thus contact with the abdomen can be assumed to have occurred.

According to a further set of embodiments, contact may be detected based on a drop in the detected light intensity indicative of a change from: exposure of the light detector to ambient light, to: a covering of the light sensor by a surface of the abdomen.

In this example, the light source need not be activated for contact detection. Engagement with the abdomen can be detected based on a change in the light detector output alone. The controller is effectively configured to detect engagement with the abdomen based on detection of a drop in the detected light levels.

For example, in one or more embodiments, the light detector may be tuned so as to be saturated when exposed to ambient light, and wherein engagement with the abdomen is detected based on a change in the output of the light detector from a state of saturation to a state of non-saturation.

Examples in accordance with a further aspect of the invention provide a method for initializing or configuring an apparatus for monitoring uterine contractions of a subject, the apparatus including:

a sensor unit for placement against an abdomen of the subject; and a belt component arranged for holding a contact surface of the sensor unit in place against the abdomen;

a contact sensing means adapted to detect an engagement between the contact surface of the sensor unit and the abdomen of the subject;

a force or pressure sensing means adapted to detect a force or pressure between the abdomen and the sensor unit;

the method comprising:

detecting engagement between the contact surface of the sensor unit and the abdomen, responsive to said detection, acquiring a measure of a starting pressure or force between the abdomen and the sensor unit using a force or pressure sensing means (for example included in the sensor unit), and determining whether a tension or application force of the belt component is in an optimum range by comparing said starting pressure with at least one pre-defined reference range.

The pre-defined reference range may be a reference range for the starting pressure or a derivative thereof, for example for a baseline of the starting pressure.

The controller is further adapted to monitor uterine contractions based on an output of the force or pressure sensing means, and preferably wherein the monitoring the uterine contractions is performed conditionally upon the belt tension falling within the optimum range.

According to at least one set of embodiments, the detecting engagement between the contact surface of the sensor unit and the abdomen may comprise:

sensing light received at the contact surface using a light detector, and detecting the engagement based on an output of the light detector.

According to a further aspect of the invention, there is also provided a computer program product comprising code means configured, when executed on a processor, to cause the processor to perform a method in accordance with in accordance with any example or embodiment outlined above or described below, or in accordance with any claim of this application.

These and other aspects of the invention will be apparent from and elucidated with reference to the embodiment(s) described hereinafter.

BRIEF DESCRIPTION OF THE DRAWINGS

For a better understanding of the invention, and to show more clearly how it may be carried into effect, reference will now be made, by way of example only, to the accompanying drawings, in which:

FIG. 5 illustrates an example of an optimum belt tension range, as an intersection of a number of parameters;

FIG. 6 shows a plan view of an outside of a sensor unit housing according to one or more embodiments;

FIG. 7 shows a perspective view of an apparatus in position on the abdomen of a subject in accordance with one or more embodiments;

DETAILED DESCRIPTION OF THE EMBODIMENTS

Figure 1:
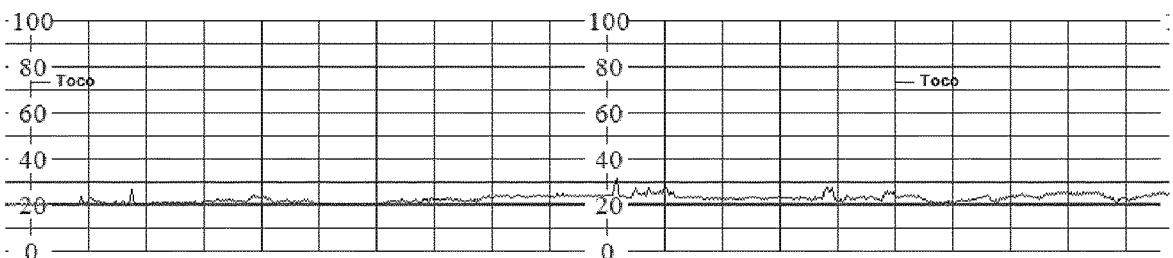
FIG. 1 shows an example pressure signal output of a tocodynamometer which has been applied with insufficient belt tension.
Figure 2:
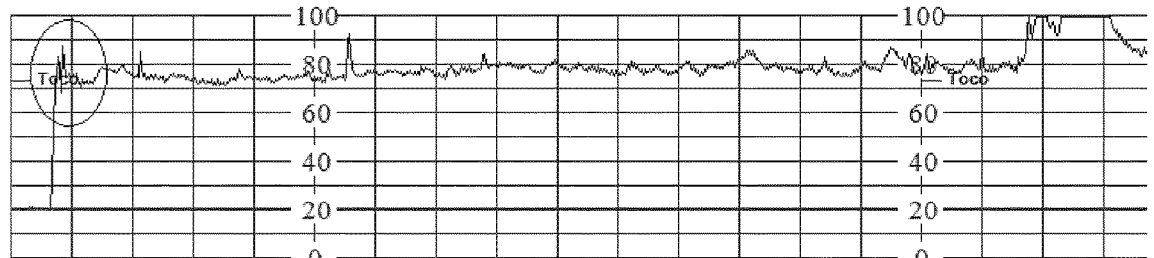
FIG. 2 shows an example pressure signal output of a tocodynamometer which has been applied with excessive belt tension.
Figure 3:
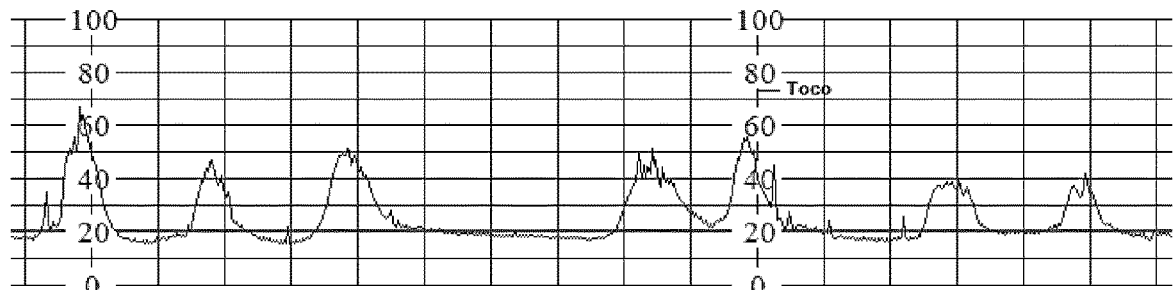
FIG. 3 shows an example pressure signal output of a tocodynamometer which has been applied with an optimum belt tension.

The invention will be described with reference to the Figures.

It should be understood that the detailed description and specific examples, while indicating exemplary embodiments of the apparatus, systems and methods, are intended for purposes of illustration only and are not intended to limit the scope of the invention. These and other features, aspects, and advantages of the apparatus, systems and methods of the present invention will become better understood from the following description, appended claims, and accompanying drawings. It should be understood that the Figures are merely schematic and are not drawn to scale. It should also be understood that the same reference numerals are used throughout the Figures to indicate the same or similar parts.

The invention provides an apparatus for use in monitoring uterine contractions and in which means are provided for separately detecting solid (e.g. flush) contact of at least a portion of the sensor unit of the apparatus on the abdomen, and for a detecting an initial starting pressure, or a baseline pressure, detected by a pressure sensor of sensor unit. A controller is arranged to first sense contact of said at least portion of the sensor unit on the abdomen, and then, responsive to said contact detection, detect the starting pressure using an integrated pressure sensor. The same pressure sensor is preferably used for monitoring the uterine contractions. The starting pressure can be used to provide a direct or indirect measure or indication of the tension of a belt which is arranged in use to hold the apparatus against the abdomen of the subject. By sensing the starting pressure, for example directly responsive to abdomen contact being sensed, this initial pressure value, or derivative thereof, can be taken as being a direct or indirect indication of the belt tension (rather than for instance caused by uterine contraction activity).

Figure 4:
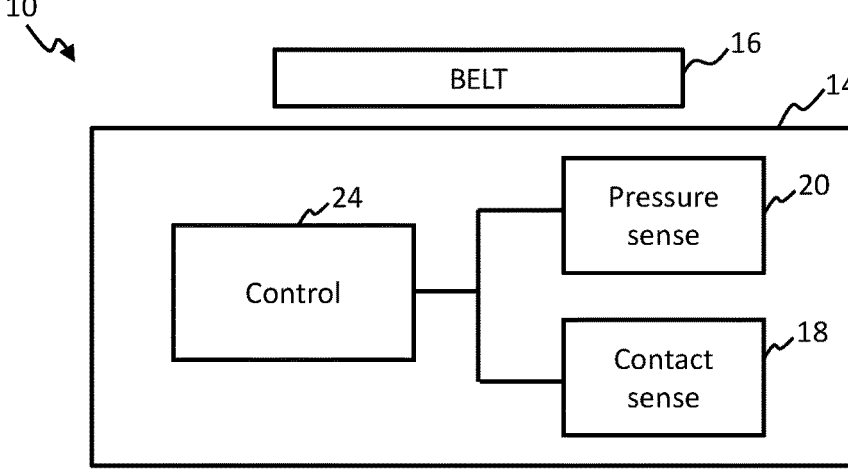
FIG. 4 shows a block diagram of parts of an example apparatus according to one or more embodiments.

FIG. 4 schematically illustrates in block diagram form the functional components of an apparatus according to one or more embodiments of the present invention.

The apparatus 10 comprises a sensor unit 14 for placement against an abdomen of the subject.

The apparatus 10 further comprises a belt component 16 arranged for holding a contact surface of the sensor unit 14 in place against the abdomen.

The apparatus 10 further comprises a contact sensing means 18 for detecting an engagement between the contact surface of the sensor unit and the abdomen of the subject.

The apparatus further comprises a force or pressure sensing means 20 adapted to detect a force or pressure between the abdomen and the sensor unit 14.

The apparatus further comprises a controller 14, adapted to perform an initialization procedure comprising:

detecting engagement between the contact surface of the sensor unit and the abdomen, responsive to said detection, acquiring a measure of a starting pressure or force between the abdomen and the sensor unit using the force or pressure sensing means, and determining whether a tension or application force of the belt component is in an optimum range based on said starting pressure and based on at least one pre-defined reference range.

The contact sensing means, the pressure sensing means and the controller may all be integrated in the sensor unit in advantageous embodiments.

The pre-defined reference range may be a reference range for the starting pressure or a derivative thereof, for example for a baseline of the measure of the starting pressure.

The acquired measure of a starting pressure may be a pressure value, or a pressure signal captured over a time window.

This pressure measurement, or a derivative thereof, can then be compared with a threshold or a reference range to assess whether it falls within an optimal operating range for the tocodynamometer, e.g. for the pressure sensing means. This comparison of the starting pressure measure or a derivative thereof with the reference range is used to determine whether the belt tension is within its optimum range.

The determined starting pressure can be used to provide a direct or indirect indication of the tension of the belt. There may be a further separate step of determining a belt tension based on the measured starting pressure, e.g. with an algorithm or conversion equation or the starting pressure itself may simply be used as a proxy measure for the further analysis. For example, the belt tension might be taken to be a baseline of the pressure measurement. This might optionally be processed with one or more conversion equations to convert it to a tension value. If there is a separate step of determining belt tension, this belt tension may be compared with said reference range instead of the starting pressure measurement itself in some examples.

Thus, according to some embodiments, the belt tension can be determined indirectly by means of the pressure measurement from the pressure sensing means. Preferably this pressure sensing means is the same pressure sensing means used by the apparatus for the measurement of the uterine contractions. A measure of the belt tension can for example be derived from the baseline of the pressure signal value of the pressure measurement (this is indicative of the mechanical force applied to the sensor without uterine contractions).

The pre-defined reference range can for example correspond to an optimum range for the belt tension in order for the pressure sensing means 20 to be operating at its optimum sensing range (where sensitivity is maximized for example).

To illustrate this, one example configuration comprising an example set of parameters will now be discussed, with reference to FIG. 5 which illustrates the intersection between the parameters.

For example, the pressure measurement sensor 20 might be capable of measuring mechanical force between 0 N and 15 N. Its optimal range (for example in which sensitivity is maximum) may be 1 N to 10 N. In this cases, the belt optimal tension might be in the range of 2 N to 9 N. Furthermore, the optimum measurement window (to enable contraction pressure variation to be fully captured) may be a pressure measurement window spanning 4 N. This would mean that a baseline for the pressure measurements must be at least 4 N lower than the upper limit of the optimal belt tension range.

The intersection of the ranges is shown in FIG. 5, and in this specific example is in the range of 2 N to 5 N. This intersection may be used as the pre-defined optimum (reference) range used by the controller 20.

The above represents just one example set-up. The precise span and magnitude of the reference range will depend upon the particular pressure sensor 20 and belt 16 which are used. It may be determined in advance and pre-stored on the controller 20. The controller might have different reference ranges stored for different apparatuses to which it is connected, and wherein the reference range can be selected by a user during set-up using a user interface.

In preferred embodiments, after the initialization procedure, the controller 24 may be configured to continue to recurrently or continuously monitor the pressure measurements to thereby recurrently or continuously monitor the belt tension. The belt tension can be determined as a baseline of the pressure measurements for example.

Preferably the controller 24 is configured to detect when the belt tension, or a baseline of the pressure sensor measurements, moves outside of a pre-defined optimum range. An early warning alert may be implemented by the controller 24, wherein it recurrently detects a trend in the belt tension, or pressure measurement baseline, and provides an alert output, e.g. for communication to a user interface, when it detects this will move outside of the reference optimum range a pre-defined time interval in the future (based on the trend).

The force or pressure sensing means 20 can take different forms. For example, it may comprise a strain gauge sensor. It may comprise an optical pressure sensing means, for example comprising a light detector and light sensor arranged in optical communication and arranged moveable relative to one another, and wherein an optical path between them varies as a function of the pressure exerted by the abdomen. For example, one of the light source and light detector may be arranged fixed relative to the abdomen, and the other may be arranged on a cantilever member which is arranged to pivot or flex based on pressure coupled directly or indirectly applied to it from the abdomen of the patient. Any other example of a pressure sensor can be used, and various options will be immediately apparent to the skilled person in this field.

FIG. 6 shows a plan view of an outside of an example implementation of the sensor unit 14. FIG. 7 (left) shows a perspective view of the sensor unit 14 attached to the patient's abdomen 32 by means of the belt 16 which wraps around the patient's abdomen and extends over the top of a housing of the sensor unit to apply a constant pressure on the sensor unit 14 inward toward the abdomen 32 to keep a lower contact surface of the sensor unit in firm contact with the abdomen. The belt may be elasticated for example. FIG. 6 (right) shows a cross-sectional view of the sensor unit 14 in place on the abdomen, with the belt 16 holding it in place. The sensor unit is thus positioned for measuring uterine contraction activity.

The sensor unit 14 may also incorporate one or more ultrasound transducer elements. These can be used to detect one or more physiological parameters of the fetus, such as fetal heart rate. Detection of fetal heart rate using Doppler ultrasound for example is a well-known technique in the field.

The controller 24 is further adapted to generate an information output indicative of whether the belt tension falls within an optimum range. It may communicate or transmit this output to a user output device for example. The user output device may for example comprise a display unit, and/or one or more other sensory output devices.

Once the initialization procedure is complete, the controller may be further adapted to monitor uterine contractions of the subject based on an output of the force or pressure sensing means 20.

Monitoring uterine contractions based on pressure measurements from a pressure sensor in a tocodynamometer type device is a well-known procedure in the field and the skilled person will know of methods for implementing this.

In advantageous embodiments, the monitoring of the uterine contractions is performed only conditionally upon a determination that the belt tension is within the optimum range. If it is not within the optimum range, uterine contraction monitoring may not be activated or may be deactivated until the belt tension is detected to be within the optimum range. This way, there is avoided generation of potentially inaccurate and thus clinically misleading uterine contraction information.

In some embodiments, responsive to the belt tension not being within the optimum range, an information output is generated for communication to a user output device for alerting a user. This may be an on-screen message for display on a display unit, for instance of a user interface device. It may additionally or alternatively comprise an auditory alert such as an alarm sound.

There are different ways to implement the contact sensing means 18, which in different embodiments can be used alone or in combination. A selection of these options will now be discussed with reference to FIGS. 8-10.

In summary, there are two broad approaches to detecting the contact. A first is to detect engagement of the sensor unit with the abdomen using the same pressure sensor integrated in the sensor unit 14 which is used to detect the pressure measurements for monitoring uterine contractions and for detection of the starting pressure (to determine belt tension). Engagement can be detected for example based on detecting a change in the measured force or pressure (an output of the pressure sensing means) which change exceeds a pre-defined threshold. Engagement may be detected based on detecting a change in a baseline of the measured force or pressure exceeding a pre-defined threshold.

For example, when the sensor unit is applied to the abdomen, there will be a relatively sudden positive shift in the baseline (or offset) of the pressure signal. This may be a step change for example or a steep inclination in the baseline exceeding a certain gradient. Thus, detection of contact with the abdomen can be detected based on detecting this shift in the baseline. The baseline can either be explicitly extracted, or its change may be detected simply by a sudden (e.g. occurring over a defined short time window) positive shift in the magnitude of the measured pressure signal values.

A threshold may be defined for the change in the baseline. The threshold may be a threshold for the magnitude of the baseline shift, and/or the gradient of the baseline shift (i.e. how steep or rapid the change in baseline occurs). One or either or both of these give an indication of contact being made, wherein the change in baseline corresponds to the initial pressure applied to the bottom of the sensor unit 14 by the abdomen. For example, if the baseline shift is above x Newton, where x is a pre-defined value, the sensor unit can be regarded as "detected on the abdomen". The threshold can be determined and pre-stored on the sensor unit controller 24 in advance for example, for instance based on empirical measurements, or analytical calculations.

A second approach to detecting the engagement with the abdomen is to include in the sensor unit 14 a separate sensor arrangement to detect the contact. With regards to this approach there are again different options.

Figure 8:
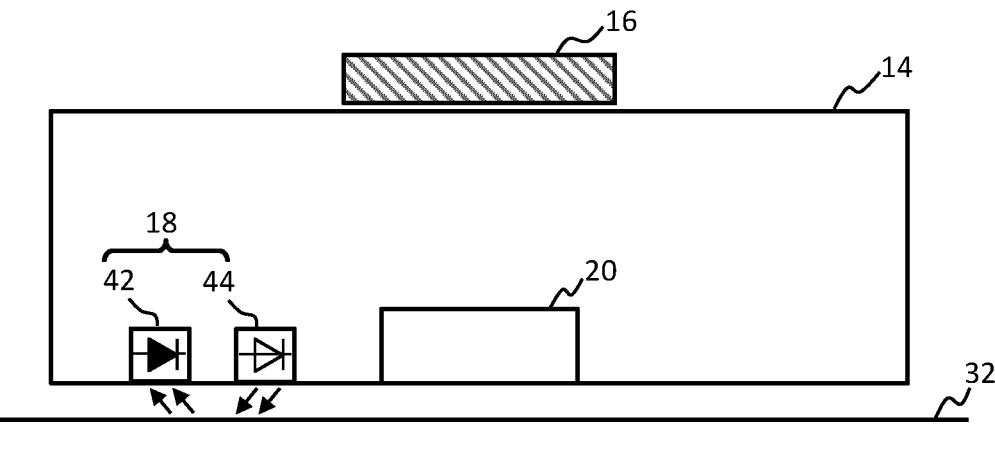
FIGS. 8 and 9 show example apparatuses which incorporate an optical sensing arrangement for detecting contact with the abdomen.
Figure 9:
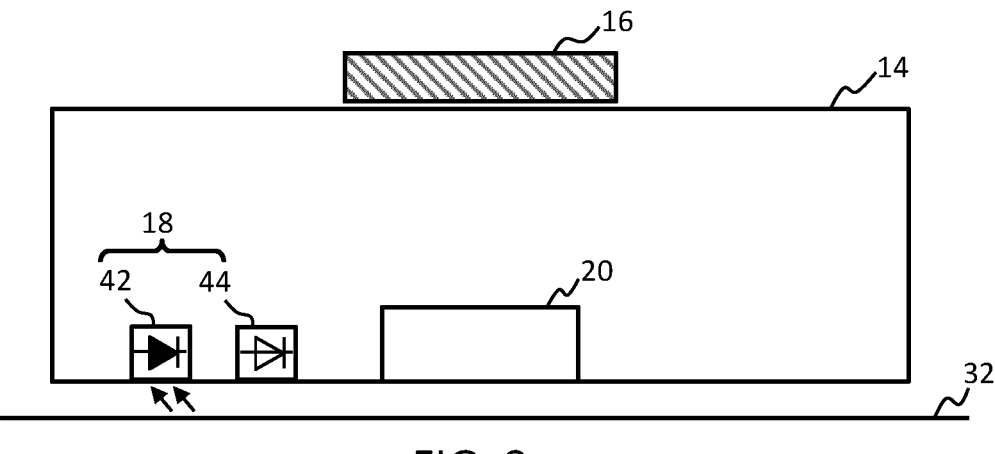

One option is to use an optical contact sensing means. FIGS. 8 and 9 schematically illustrate cross-sectional views of example apparatuses 10 which incorporate such an optical sensing means 18. Note, for simplicity, the controller 24 is not shown, but this is also included in the sensor unit 14 operatively coupled with the pressure sensing means 20 and the contact sensing means 18.

In both of the embodiments of FIGS. 8 and 9, the contact sensing means 18 comprises an optical sensor arrangement comprising a light source 44 arranged to direct a light output from a (lower) contact surface of the sensor unit 14 into the skin of the abdomen 32 of the subject and a light detector 42 arranged to detect said light output at the contact surface after passage through the skin, and wherein the contact sensing means is provided by the optical sensor arrangement, contact being detected based on an output of the light detector 42.

By way of example, the light source may be an infrared light (IR) source and the light detector an infrared light detector. However, visible light may alternatively be used.

The light source 44 may be an LED in some examples, though this is not essential. The light detector 42 may comprise one or more photodiodes.

In advantageous embodiments, the same optical sensor arrangement 18 may be used for measuring maternal pulse rate. The sensor unit 14 for example may incorporate an integrated optical sensor arrangement for the purpose of detecting pulse rate, and the controller 24 may be arranged to utilize this same sensor for the secondary or dual purpose of detecting contact. This would minimize parts in the apparatus and thus reduce overall size and manufacturing complexity of the apparatus.

For example, the optical sensor arrangement may be a PPG sensor integrated in the unit for determining pulse, the PPG sensor comprising the light source 44 arranged to direct a light output from said contact surface into the skin of the subject and a light detector 42 arranged to detect said light output at the contact surface after passage through the skin 32.

For example, the optical sensor arrangement may comprise an infrared (IR) transmitter 44 and receiver 42 pair that can be used to determine the maternal pulse. The transmitter may comprise an LED for example. The receiver may be or comprise a photodiode for example. The IR light source 44 illuminates the abdomen 32 skin and the photodiode 42 receives the light reflected from the skin, thus measuring the changes in the light absorption, which correspond to blood volume changes. These blood volume changes (e.g. a frequency of the blood volume variation) are indicative of the maternal pulse.

In some embodiments for example, detection of contact with the abdomen may be based on the controller detecting a maternal pulse with the optical sensor arrangement. Thus, the detection of maternal pulse may be a criterion for detection of the Toco sensor contact on the abdomen.

There are different ways of using an optical sensing means such as that outlined above to detect contact.

In one set of embodiments, contact may be detected based on detection of the light output generated by the light source 44 at the light detector 42. When this is detected, it means that the optical sensor element must be in optical communication with the skin for the light to have coupled through the tissue of the subject to the light detector, and thus contact with the abdomen can be assumed to have occurred. This example is illustrated in FIG. 8.

In a further set of embodiments, contact may be detected based on use of an output of the light detector 42 alone. For example contact may be detected based on detecting a drop in the detected light intensity at the light detector, and where for example this drop is of a magnitude which is indicative of a change from: exposure of the light detector to ambient light, to: a covering of the light sensor by a surface of the abdomen.

For example, the light detector 42 may be tuned so as to be saturated when exposed to ambient light, and wherein contact is detected based on a change in the output of the light detector 42 from a state of saturation to a state of non-saturation.

Figure 10:
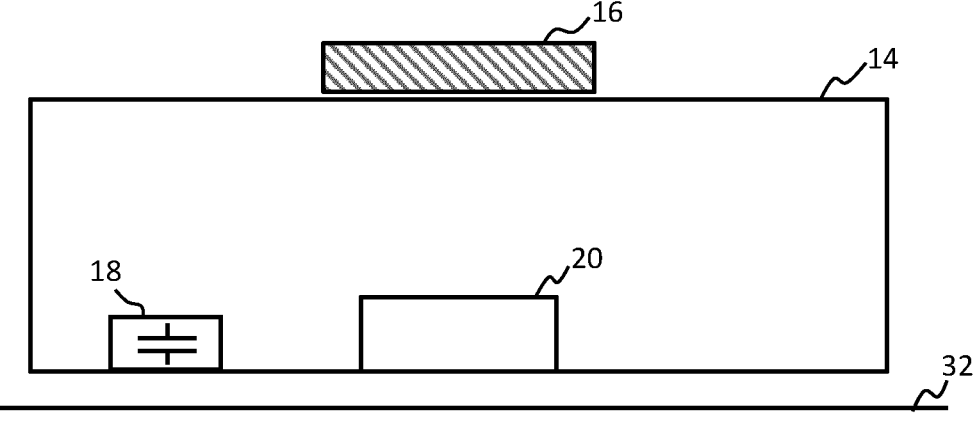
FIG. 10 shows an example apparatus which incorporates a capacitive sensing element for detecting contact with the abdomen.

According to a further set of embodiments, the contact sensing means may comprise a capacitive sensor 18 element arranged to capacitively detect contact between the lower contact surface of the sensor unit 14 and the abdomen surface. This example is illustrated in FIG. 10.

Further methods to detect the contact with the abdomen might include, by way of non-limiting example: a mechanical switch (contact is detected by mechanical depression of a switch or button integrated exposed at the contact surface), a temperature sensor (contact is detected based on a detected elevation in temperature by a certain amount or to a certain value or range), an electrical conductivity sensor, and/or an optical proximity sensor. In each case, the sensor may have a sensitive [art exposed at the contact surface of the sensor unit 14. A combination of different contact sensing methods is also possible.

According to a further aspect of the invention, there may further be provided a user interface unit for providing a sensory output of the results of the initial pressure detection and/or of a belt tension. This may take the form for instance of a monitoring unit or monitoring station comprising at least a display device for displaying information related to the detected initial belt tension, and/or analysis performed by the controller. Preferably it may further comprise a user input means for the user to input control commands for the apparatus, e.g. to re-check the belt tension, and/or to override various functions of the controller, or to adjust parameters used by the controller, e.g. the pre-defined optimal range for the detected belt tension.

A monitoring unit may for example be a fetal monitoring unit, which may in some examples be configured to display a plurality of measurement information related to the fetus and the mother (e.g. fetal and maternal heart rate, blood pressure, temperature, and/or contraction activity, as well as belt tension) and may receive sensor inputs from a range of different physiological sensor sources.

In some examples, a belt tension indicator may be displayed on a display unit of the monitoring device, which may be a graphic or textual indicator in different examples. This may indicate a real-time estimated value of the belt tension for example. The belt tension indicator may display the belt tension graphically in the form of a linear graphical scale which marks the optimum range for the belt tension within the scale, so that the operator (e.g. clinician) can easily see when belt tension is close to moving outside of the optimum range.

In some examples, the sensor unit 14 may comprise a visual indictor arranged to be visible at an exterior surface of a housing of the sensor unit 14, and configured to provide a visual indication of the current belt tension, and/or whether the belt tension is within an optimum range. The visual indicator may comprise a number of colored lights (e.g. LEDs) for example. The different colors may be used to indicate different grades or levels of belt tension, e.g. first color (tension too low), second color (tension within optimum range), third color (tension too high). The first, second and third colors could be blue, green and red for example. This represents one example only which does not limit the invention.

The monitoring unit or the sensor unit may be adapted to generate an acoustic or visual signal to alert a user when belt tension moves outside of the optical range and thus needs adjustment. For example, an alarm might be sounded.

Examples in accordance with a further aspect of the invention provide a method for initializing an apparatus for monitoring uterine contractions of a subject, the apparatus including:

a sensor unit for placement against an abdomen of the subject; and a belt component arranged for holding a contact surface of the sensor unit in place against the abdomen;

the method comprising:

detecting engagement between the contact surface of the sensor unit and the abdomen, responsive to said detection, acquiring a measure of a starting pressure or force between the abdomen and the sensor unit using a force or pressure sensing means, and determining whether a tension or application force of the belt component is in an optimum range based on said starting pressure and based on at least one pre-defined reference range.

The pre-defined reference range may be a range for the starting pressure or a derivative thereof, for example a baseline of the starting pressure.

Implementation options and details for each of the above steps may be understood and interpreted in accordance with the explanations and descriptions provided above for the apparatus aspect of the present invention (i.e. the apparatus aspect).

Any of the examples, options or embodiment features or details described above in respect of the apparatus aspect of this invention (in respect of the apparatus) may be applied or combined or incorporated mutatis mutandis into the present method aspect of the invention.

The method may further comprise monitoring uterine contractions based on an output of the force or pressure sensing means, wherein the monitoring the uterine contractions is performed conditionally upon a determination that the belt tension lies within the optimum range.

The detecting engagement between the contact surface of the sensor unit and the abdomen may comprise:

sensing light received at the contact surface using a light detector, detecting the engagement based on an output of the light detector.

Figure 11:
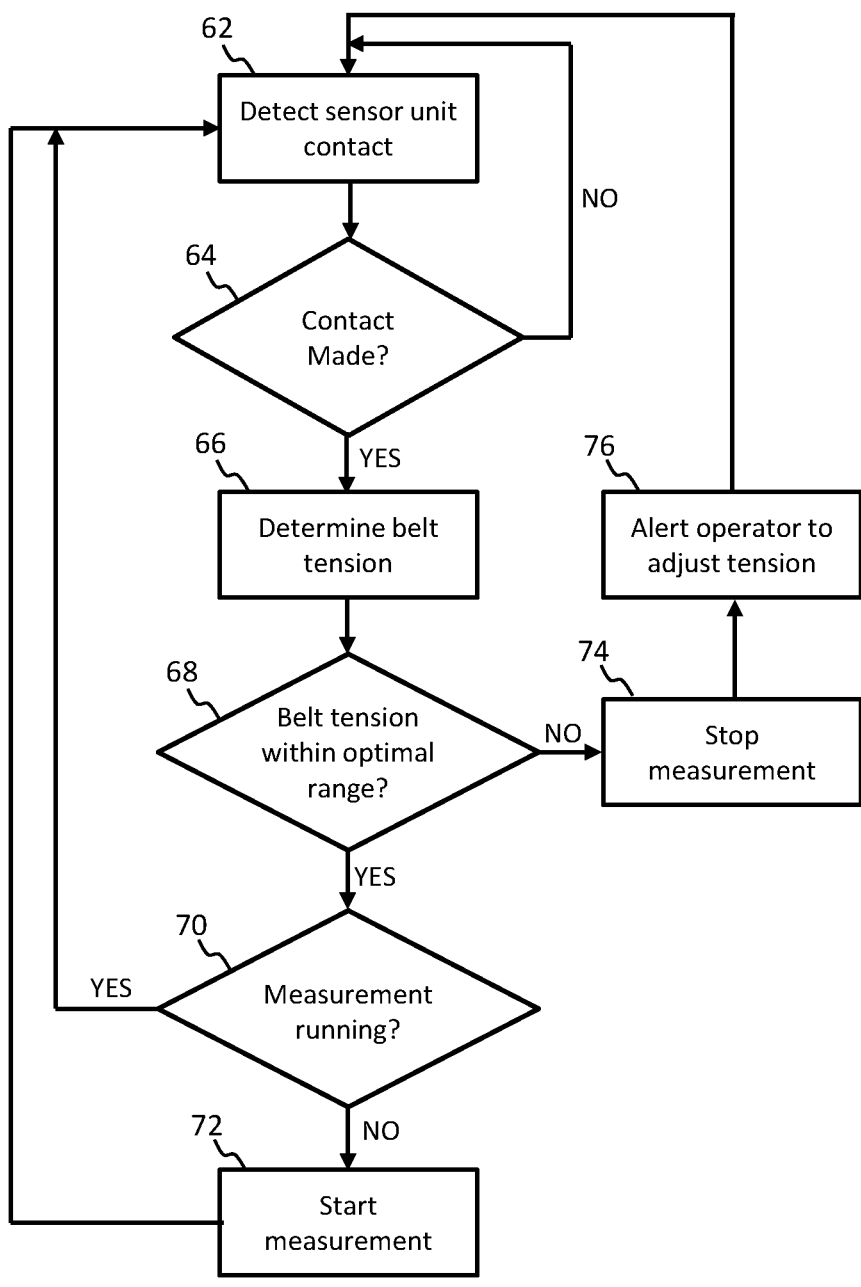
FIG. 11 outlines in block diagram form an example workflow according to one or more embodiments.

By way of illustration of the, one example workflow according to one or more embodiments is outlined in FIG. 11.

A contact sensing means 18 is arranged to detect 62 contact between the sensor unit 14 and the abdomen, for example using one or more of the approaches outlined above. A controller may recurrently or continuously monitor signals from the contact sensing means and check 64 whether contact has been made. As soon as contact is made, a tension of the belt is determined 66 based on acquiring an initial or starting measurement from a pressure sensing means integrated in a contact sensing face of the sensor unit. For example, belt tension may be taken as the baseline of a pressure signal output from the pressure sensing means immediately responsive to detecting contact. Additionally or alternatively, an algorithm or conversion equation may be applied to convert the measured pressure, or baseline pressure, into a belt tension value.

A determination 68 is made as to whether the belt tension falls within a defined belt tension range. This can be done in different ways. A value of the belt tension can be calculated from the initial pressure measurement and this compared with a pre-defined reference range for the belt tension. Alternatively, a reference range may be pre-defined for the initial pressure measurement itself, or baseline of the initial pressure measurement, where this reference range has been calculated in advance such that an initial pressure measure falling within this range means that the belt tension is within its optimum range.

If the belt tension is determined 68 to be outside of an optimum range, measurement of contractions by the apparatus is stopped 74 and an alert message (e.g. visual or auditory) can be generated to alter a user that they need to adjust the belt tension. The belt tension may be displayed on a display unit for an operator to view. The workflow then returns to a starting step, in which contact with the sensor unit is redetected 62 before another starting measurement of the pressure is re-acquired to check again the belt tension.

This loop continues until a determination 68 is made that the belt tension lies within the optimum range. At this point, measurement and monitoring of uterine contractions using the pressure sensing means 20 in the sensor unit 14 can proceed. A check 70 is made as to whether contraction measurements are already being performed, in which case they can continue, and the workflow returns to the step of checking contact and re-checking belt tension. If not, then the contraction measurement is activated 72 and the workflow at this point returns to the beginning 62. In this way, in either case, the workflow recurrently or continuously re-checks the belt tension even after measurements have started to determine if it is still within the optimum rage. If it any point it falls outside the range, measurements cease 74 until the tension is adjusted.

Optionally, an early function might be included such that an early warning is issued if the belt tension approaches the edge of the optimal tension range, for example within a pre-defined proximity or threshold of either the upper or lower boundary of the optimal tension range.

Examples in accordance with a further aspect of the invention also provide a computer program product comprising code means configured, when executed on a processor, to cause the processor to perform a method in accordance with any example or embodiment outlined above or described below, or in accordance with any claim of this application.

As discussed above, embodiments make use of a controller 20. The controller can be implemented in numerous ways, with software and/or hardware, to perform the various functions required. A processor is one example of a controller which employs one or more microprocessors that may be programmed using software (e.g., microcode) to perform the required functions. A controller may however be implemented with or without employing a processor, and also may be implemented as a combination of dedicated hardware to perform some functions and a processor (e.g., one or more programmed microprocessors and associated circuitry) to perform other functions.

Examples of controller components that may be employed in various embodiments of the present disclosure include, but are not limited to, conventional microprocessors, application specific integrated circuits (ASICs), and field-programmable gate arrays (FPGAs).

In various implementations, a processor or controller may be associated with one or more storage media such as volatile and non-volatile computer memory such as RAM, PROM, EPROM, and EEPROM. The storage media may be encoded with one or more programs that, when executed on one or more processors and/or controllers, perform the required functions. Various storage media may be fixed within a processor or controller or may be transportable, such that the one or more programs stored thereon can be loaded into a processor or controller.

Variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality.

A single processor or other unit may fulfill the functions of several items recited in the claims.

The mere fact that certain measures are recited in mutually different dependent claims does not indicate that a combination of these measures cannot be used to advantage.

A computer program may be stored/distributed on a suitable medium, such as an optical storage medium or a solid-state medium supplied together with or as part of other hardware, but may also be distributed in other forms, such as via the Internet or other wired or wireless telecommunication systems.

If the term "adapted to" is used in the claims or description, it is noted the term "adapted to" is intended to be equivalent to the term "configured to".

Any reference signs in the claims should not be construed as limiting the scope.

The invention claimed is:

1. An apparatus for monitoring uterine contractions of a subject, the apparatus comprising:
   a sensor for placement against an abdomen of the subject, the sensor comprising:
      a contact sensor configured to detect an engagement between a contact surface of the sensor and the abdomen of the subject; and
      a force or pressure sensor configured to detect a force or pressure between the abdomen and the sensor;
   a belt component configured to hold the contact surface of the sensor in place against the abdomen; and
   a controller, configured to perform a procedure comprising:
      receive an indication of engagement between the contact surface of the sensor and the abdomen from the contact sensor,
      responsive to receiving said indication, acquiring a measure of a starting pressure or force between the abdomen and the sensor using the force or pressure sensor, and
      determining whether a tension or application force of the belt component is in an optimum range by comparing said starting pressure or force between the abdomen and the sensor with at least one pre-defined reference range.

2. The apparatus as claimed in claim 1, the controller further configured to generate an information output indicative of whether the belt tension is within the optimum range, and communicating the output to a user output device.

3. The apparatus as claimed in claim 1, wherein the controller is further configured to monitor uterine contractions based on an output of the force or pressure sensor.

4. The apparatus as claimed in claim 3, wherein the monitoring the uterine contractions is performed conditionally upon the belt tension being within the optimum range.

5. The apparatus as claimed in claim 1, wherein, responsive to a determination that the tension force of the belt component is not within the optimum range, the controller is configured to generate an output for communication to a user output device for alerting a user.

6. The apparatus as claimed in claim 1, wherein the sensor further comprises an optical sensor arrangement comprising a light source configured to direct a light output from said contact surface into the skin of the subject and a light detector configured to detect said light output at the contact surface after passage through the skin, and wherein the detection of the engagement between the contact surface of the sensor and the abdomen of the subject is based on an output of the light detector.

7. The apparatus as claimed in claim 6, wherein the detection of the engagement between the contact surface of the sensor and the abdomen is based on detection at the light detector of the light output generated by the light source.

8. The apparatus as claimed in claim 6, wherein the detection of the engagement between the contact surface of the sensor and the abdomen is based on a drop in the detected light intensity indicative of a change from exposure of the light detector to ambient light to a covering of the light detector by a surface of the abdomen.

9. The apparatus as claimed in claim 8, wherein the light detector is tuned so as to be saturated when exposed to ambient light, and wherein the detection of the engagement between the contact surface of the sensor and the abdomen is based on a change in the output of the light detector from a state of saturation to a state of non-saturation.

10. The apparatus as claimed in claim 6, wherein the optical sensor arrangement comprises a PPG sensor, and wherein the controller is adapted to determine a pulse of the subject using an output of the PPG sensor.

11. The apparatus as claimed in claim 1, wherein the contact sensor is provided by the same component as the force or pressure sensing means, and wherein engagement is detected based on detecting a change in the measured force or pressure exceeding a pre-defined threshold.

12. A method for initializing or configuring an apparatus for monitoring uterine contractions of a subject,
   the apparatus comprisingg:
      a sensor for placement against an abdomen of the subject, the sensor comprising:
         a contact sensor configured to detect an engagement between a contact surface of the sensor and the abdomen of the subject; and
         a force or pressure sensor configured to detect a force or pressure between the abdomen and the sensor; and
      a belt component configured to hold the contact surface of the sensor in place against the abdomen;
      a controller adapted to perform the method,
   the method comprising:
      detecting engagement between the contact surface of the sensor and the abdomen,
      responsive to said detection, acquiring a measure of a starting pressure or force between the abdomen and the sensor using the force or pressure sensor, and
      determining whether a tension or application force of the belt component is in an optimum range by comparing said starting pressure or force with at least one pre-defined reference range.

13. The method as claimed in claim 12, further comprising monitoring uterine contractions based on an output of the force or pressure sensor, wherein the monitoring the uterine contractions is performed conditionally upon a determination that the belt tension lies within the optimum range.

14. The method as claimed in claim 12, wherein the detecting engagement between the contact surface of the sensor and the abdomen comprises:

sensing light received at the contact surface using a light detector, and detecting the engagement based on an output of the light detector.

15. A non-transitory computer program product comprising code means configured, when executed on a processor, to cause the processor to perform the method in accordance with claim 12, wherein the method utilizes the apparatus.

\* \* \* \* \*